United States Patent [19]

Kötzsch et al.

[11] 4,404,014
[45] Sep. 13, 1983

[54] SALT-LIKE PRODUCTS OF THE ADDITION OF PHENOLS ONTO AMINO ORGANOSILANE ESTERS AND METHOD FOR THE PREPARATION THEREOF AND USE AS A PRESERVATIVE

[75] Inventors: Hans-Joachim Kötzsch; Hans-Joachim Vahlensieck, both of Rheinfelden, Fed. Rep. of Germany

[73] Assignee: Dynamit Nobel AG, Troisdorf, Fed. Rep. of Germany

[21] Appl. No.: 173,543

[22] Filed: Jul. 30, 1980

Related U.S. Application Data

[62] Division of Ser. No. 90,725, Nov. 2, 1979, Pat. No. 4,254,270.

Foreign Application Priority Data

Nov. 2, 1978 [DE] Fed. Rep. of Germany ....... 2847400

[51] Int. Cl.³ .................... A01N 31/08; A01N 55/00
[52] U.S. Cl. .......................................... 71/67; 424/184; 71/79; 71/106; 71/122; 106/15.05; 106/287.15; 106/287.16
[58] Field of Search ................. 71/67, 79, 122, 106; 424/184; 556/413

References Cited

U.S. PATENT DOCUMENTS

| | | | |
|---|---|---|---|
| 2,253,762 | 8/1941 | Carswell et al. | 71/67 |
| 2,400,677 | 5/1946 | Allen | 71/67 |
| 2,784,139 | 3/1957 | Cutler | 424/184 |
| 2,935,475 | 5/1960 | Bernard | 556/402 |
| 3,730,701 | 5/1973 | Isquith et al. | 71/67 |
| 3,794,736 | 2/1974 | Abbott et al. | 424/184 |
| 3,817,739 | 6/1974 | Abbott et al. | 71/67 |
| 3,940,430 | 2/1976 | Brenner et al. | 424/184 |
| 4,254,270 | 3/1981 | Kotzsch et al. | 71/67 |

*Primary Examiner*—Glennon H. Hollrah
*Attorney, Agent, or Firm*—Sprung, Horn, Kramer & Woods

[57] ABSTRACT

An adduct of phenol with an aminoorganosilane ester with salt-like charge-transfer-complex structure of the general formula

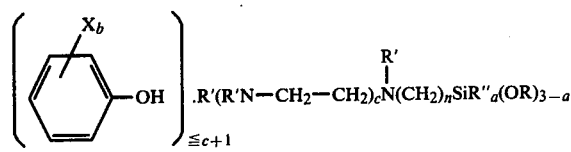

wherein
R represents an alkyl moiety of 1 to 8 carbon atoms or ethylene glycol or polyethylene glycol or propylene glycol or polypropylene glycol moieties terminally closed with a lower alkyl or acyl group;
R' represent hydrogen or alkyl moieties having 1 to 20 carbon atoms optionally containing one or more ether bridges, a cycloalkyl moiety or an aryl moiety;
R" represents alkyl with 1 to 8 carbon atoms;
X represents halogen or $C_{1-14}$ alkyl moieties or a nitro group;
a being a value of 0 to 3;
b a value of 0 to 5;
c a value of 0 to 20; and
n a value of 1 to 6;

and a process for preparing the same.

46 Claims, No Drawings

SALT-LIKE PRODUCTS OF THE ADDITION OF PHENOLS ONTO AMINO ORGANOSILANE ESTERS AND METHOD FOR THE PREPARATION THEREOF AND USE AS A PRESERVATIVE

This is a division of application Ser. No. 090,725, filed Nov. 2, 1979.

BACKGROUND OF THE INVENTION

1. Field of the Invention

The subject matter of the present invention is salt-like charge transfer complex compounds of phenols with amino organosilane esters of the general formula:

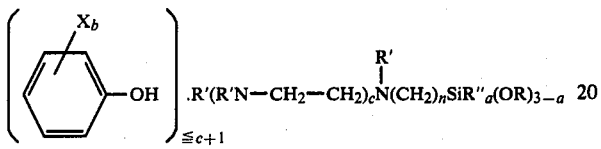

wherein
- R represents an alkyl moiety of 1 to 8 carbon atoms or ethylene glycol or polyethylene glycol or propylene glycol or polypropylene glycol moieties terminally closed with a lower alkyl or acyl group;
- R' represent hydrogen or alkyl moieties having 1 to 20 carbon atoms optionally containing one or more ether bridges, a cycloalkyl moiety or an aryl moiety;
- R" represents alkyl with 1 to 8 carbon atoms;
- X represents halogen or $C_{1-4}$ alkyl moieties or a nitro group;
- a being a value of 0 to 3;
- b a value of 0 to 5;
- c a value of 0 to 20; and
- n a value of 1 to 6.

Further subject matter of the present invention is a method of preparing these new compounds as well as the use of these compounds as insecticidal and biocidal substances.

2. Discussion of the Prior Art

It is known that phenols, alkylphenols, nitrophenols, and especially polychlorophenols have biocidal and insecticidal effects. It is disadvantageous in these known phenol derivatives that their vapor pressure is too high, so that their biocidal action diminishes in the course of time. Also, the vapors of these compounds which escape into the atmosphere because of the high vapor pressure constitute an undesirable pollution of the environment which can only be reduced by appropriate proceedings.

Attempts have been made to use biocidal phenols, especially pentachlorophenol, in the form of their salts with various amines, as preservative ingredients. The phenols, however, remain volatile in the presence of water vapor. Furthermore, such dressings are not resistant to solvents and oils and cause color alterations.

Even the silane esters of chlorophenols, which are described in U.S. Pat. No. 3,940,430, have the disadvantage named above. Their vapor pressure is still too high; furthermore, they are liable to hydrolysis, so that when used in a damp atmosphere, the corresponding phenols are gradually released, resulting, again, in the disadvantages cited above.

SUMMARY OF THE INVENTION

The problem therefore existed of combining phenols and their derivatives in a compound that is resistant to hydrolysis, has a low vapor pressure, has a long endurance, and produces an effect at least equal to that of the known phenols and phenol derivatives.

As a solution to this problem, salt-like charge transfer complexes of phenols with amino organosilane esters have now been found, which correspond to the formula

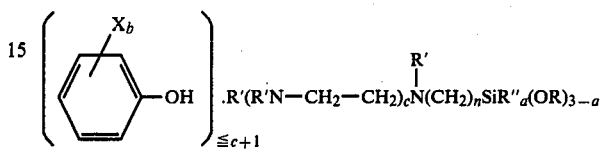

wherein
- R represents an alkyl moiety of 1 to 8 carbon atoms or ethylene glycol or polyethylene glycol or propylene glycol or polypropylene glycol moieties terminally closed with a lower alkyl or acyl group;
- R' represents hydrogen or alkyl moieties having 1 to 20 carbon atoms optionally containing one or more ether bridges, a cycloalkyl moiety or an aryl moiety. When R' is a cycloalkyl moiety, it preferably has 4 to 7 carbocyclic carbon atoms;
- R" represents alkyl with 1 to 8 carbon atoms;
- X represents halogen or $C_{1-4}$ alkyl moieties or a nitro group;
- a being a value of 0 to 3;
- b a value of 0 to 5;
- c a value of 0 to 20; and
- n a value of 1 to 6, preferably 1 to 3.

The preparation of the new compounds is characterized in that phenols of the general formula

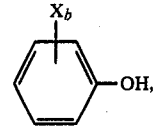

wherein
X and b have the meanings given above, in amounts which are stoichiometric or less than stoichiometric with respect to the amine nitrogen present in the amino organosilane ester, are contacted in the substantial absence of water with an amino organosilane ester of the general formula

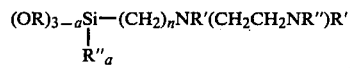

wherein
R, R', R", a, n, and c have the meanings defined above, while maintaining a temperature between $-40°$ C. and $+60°$ C.

If the method of preparation of this invention is practiced at temperatures above the limit of 60° C., the substances of the invention can likewise be obtained. When a temperature of approximately 100° C. is used do transesterification rates of 1 to 8% occur within 200 hours. These results are obtained also by proceeding in the absence of a catalytically acting amine pursuant to the method of U.S. Pat. No. 3,940,430.

What takes place in the process of the invention is unexpected because the aminosilane ester components always present in the reaction system are in every case primary, secondary or tertiary amines which, according to the former state of knowledge, produce a transesterification with the phenols on the silicon atom, which takes place with condensation. On the basis of the amine function of the aminosilane ester components and the knowledge of the catalytic effect of amines, which is confirmed by comparative tests, the condensative transesterification in accordance with the process described in U.S. Pat. No. 3,940,430 suggested itself to the technical expert and was to be expected by him as the result of the reaction. The formation of the salt-like charge transfer complex compounds of the invention—hitherto unknown substances having substantially different properties—is therefore surprising.

The process for the preparation of the new compounds of the invention is performed in a liquid medium free of water. No catalytically active amine is added as catalyst. The components are combined in such amounts that there will be one mole or less than one mole of the phenol for each amine nitrogen in the aminosilane ester. The phenol can also be present during the reaction in an excess above this stoichiometric amount, without impairing the reaction.

It is desirable to proceed by placing the first component, preferably the phenol, into the reaction vessel and then stirring the second component, preferably the aminosilane ester, into it. The reaction then takes place spontaneously and with a slight yield of heat. On account of the exothermy of the reaction, the addition of the second component to the first is to be performed such that the temperature does not exceed 60° C. This can be accomplished by cooling the mixture thoroughly during the reaction or by adding the second component to the first in portions in such a manner as to avoid excessive heating.

The use of a solvent may contribute to the removal of the heat of the reaction. The use of a solvent is furthermore recommendable when one of the two reactants is in solid form or the reaction product is a solid. It is not necessary that the starting product dissolve completely in the solvent. Even when one of the starting products is only in suspension, the reaction of the invention takes place with the formation of the addition product.

Examples of solvents which have proven usable for the performance of the process of the invention are: hydrocarbons such as pentane, hexane, heptane, isooctane, cyclohexane, benzene, toluene and benzine fractions, chlorinated hydrocarbons such as methylene chloride, chloroform, carbon tetrachloride, trans-dichloroethylene, trichloroethylene, perchloroethylene, chlorobenzene and dichlorobenzene, ethers such as diisopropyl ether, tetrahydrofuran, dioxane and ethylene glycol dimethyl ether, and other neutral, nonaqueous liquids such as alcohols (preferably of the same type as the alcohol group contained in the silane ester component), ketones, esters, amides and others which must have neither acid nor basic properties and must be removable by evaporation or washing.

The reaction time is usually less than one hour; the reaction can be slightly retarded, however, to allow for removal of the heat of reaction. The reaction time depends only on the rate of addition of the second component, and is controlled by that rate. Even components (pentachlorophenol for example) which are used in suspension react rapidly and easily in accordance with the process of the invention by passing smoothly into solution as the reaction progresses. This additional dissolution process may involve a slight retardation which does not, however, adversely affect the process of the invention.

The substances of the invention are in some cases liquid at standard temperature, and in others they are well-crystallized substances of varying solubility. Liquid substances are preferably prepared without the use of solvents. In this case no refining is necessary because if pure starting components are used, these substances are obtained in pure form after the end of the reaction in a virtually 100% yield. The preparation of crystallizing substances is performed preferably in solvents so as to assure thorough mixing to control the reaction. The achievement of a homogeneous solution is not necessary, since the reactions can in any case be performed with complete transformation even if the substance is in suspension, resulting in yields of virtually 100%.

The isolation of the reaction products from suspensions can be performed by filtration or centrifugation, for example. However, the evaporation of the solvent followed by drying, in vacuo in some cases, has proven always to be especially advantageous. If pure starting components are used, pure substances are regularly obtained by this method. If impure raw materials must be used, pure products can be obtained simply by applying the conventional methods of recrystallization.

Examples of suitable starting substances are phenol, o- and p-cresol, 4-isopropylphenol, thymol, o-, m- and p-chlorophenol, 2,4-dichlorophenol, 2,4,5-trichlorophenol, 2,4,5,6-tetrachlorophenol, pentachlorophenol, p-bromophenol, 3,5-dibromophenol, pentabromophenol, pentafluorophenol, p-iodophenol, o-, m- and p-nitrophenol, 2,4-dinitrophenol, and picric acid, in mixtures if desired.

Examples of suitable amino organosilane ester components are N,N-dimethylaminomethyldimethylethoxysilane, N-n-butylaminomethylmethyldimethoxysilane, N-methylaminomethyldimethyl-ω-methoxyethoxyethoxyethoxysilane, N-cyclohexylaminomethyldimethylmethoxysilane, N-dodecylaminomethyltrimethoxysilane, N,N-bis-(2-methoxyethyl)-aminomethyldimethyl-2-methoxyethoxisilane, 2-[N(aminoethyl)-amino]ethyltriethoxysilane, 3-aminopropyltrimethoxysilane, 3-aminopropyltriethoxysilane, 3-N,N-dimethylaminopropyltrimethoxysilane, 3-aminopropyltrimethoxyethoxysilane, 3-(N-methylamino)propyltrimethoxysilane, 3-N,N-dibutylaminopropyltrimethoxysilane, 3-(N-dodecylamino)propyltrimethoxysilane, 3-[N-(β-aminoethyl)amino]propyltriethoxysilane, 3-[N-(2'-β-aminoethylaminoethyl)amino]propyltriethoxysilane, 3-(ω-aminododecaethyleneimino)propyltriethoxysilane, 3-aminopropylmethyldiethoxysilane and 3-(N-methylamino)propylmethyldimethoxysilane, in mixtures if desired.

This enumeration shows that a great number of compounds can be used as starting products; if the aminosilane ester contains polyethyleneimino groups (i.e., when, in the above general formula, c assumes values greater than 1), mixtures of higher polyethyleneimines of different length can be incorporated so that c can also represent fractional numbers.

Similar considerations apply to the ester moiety on the silicon atom when it consists of polyethylene or polypropyleneglycol moieties. Here, again, the ester groups can contain mixtures.

The aminosilane esters add onto the phenolic compounds by forming a hydrogen bridge. In fact, each amino nitrogen can form, with quaternation, a phenol molecule in the form of a hydrophenolate of the nature of a deformed, salt-like charge transfer complex.

For example, 3-N,N-dimethylaminopropyltrimethoxysilane and pentabromophenol add quantitatively to form 3-N,N-dimethylaminopropyltrimethoxysilane hydropentabromophenolate; other examples are given in the following structural formulas:

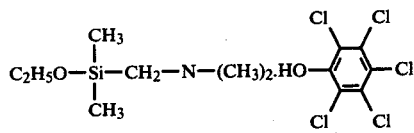
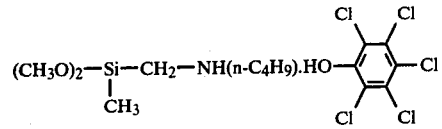
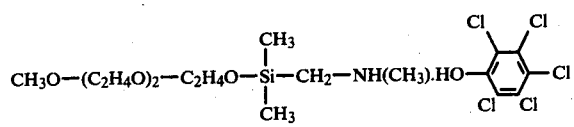
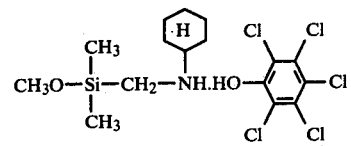
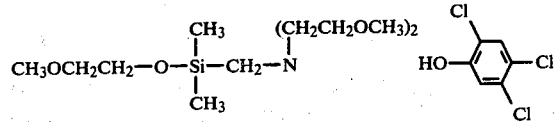
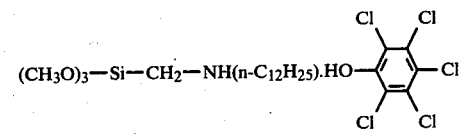
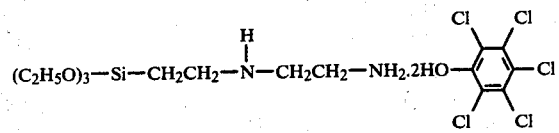
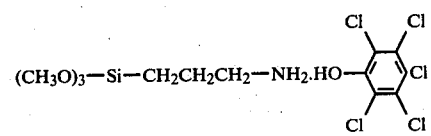
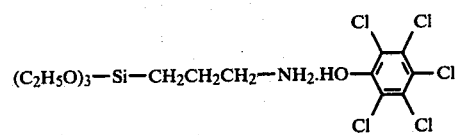
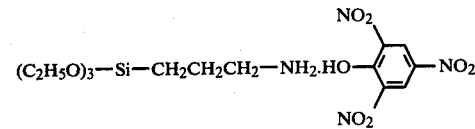
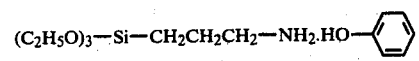
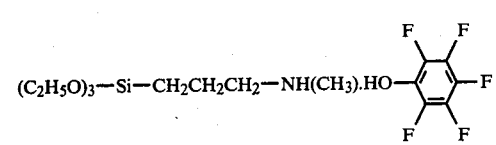
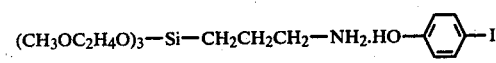
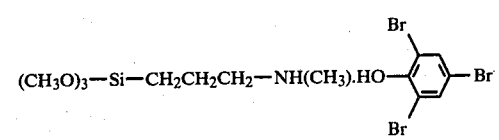
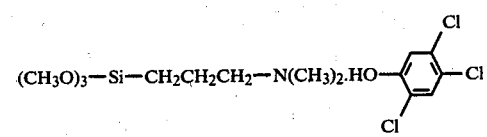
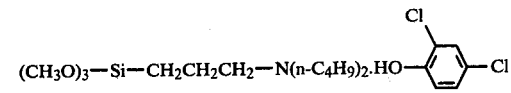
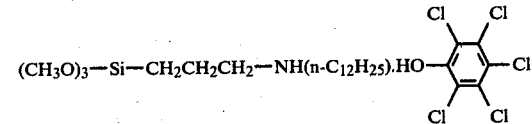
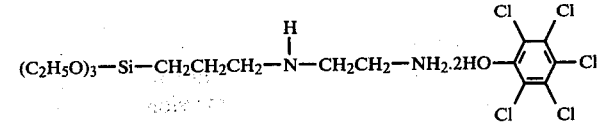

-continued

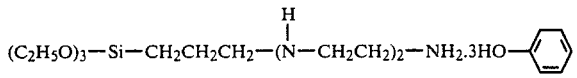

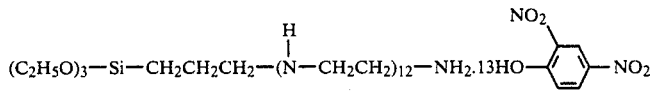

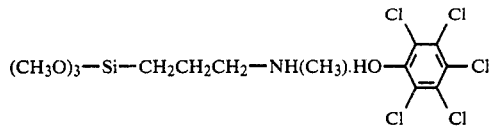

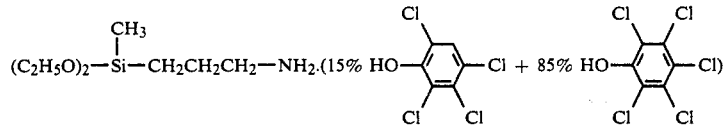

The substances of the invention have a biocidal action against fungi, bacteria, viruses, microphytes, insects and other microorganisms, such as mollusks, and this action is graded according to the phenol used. It has been found in more precise studies that the biocidal activity of several substances of the invention is in some cases considerably greater than that of the phenols on which they are based, including that of their silane esters, as proven especially by the lower threshold concentrations of their biocidal effects. This applies not only to chlorinated phenols but also to phenols containing nitro groups when the latter are used as wood protective agents, pest controlling means or fungicide for leather goods. Evidently the salt-like charge transfer bond mediates synergistic effects so that concentrations of as little as 0.02 to 0.2% in the substrate produce full biological protection.

Generally, the adducts of the invention are employed in an amount of at least 0.01 percent and up to 0.5 percent, preferably 0.02 to 0.2 percent.

Another advantage of the substances of the invention over the known applications of phenols or silane esters is their significantly superior surface activity, as proven by comparative diffusion tests and sprinkling tests on agar cultures. In the long-term test, too, the substances of the invention are superior to the phenols and their esters. As it is known, the preservative properties of biocidal phenols are lost relatively quickly as a result of their vapor pressure. They escape into the ambient atmosphere, and this limits their applications because they can have a polluting effect on the environment. This is true, though to a lesser extent, of the silyl esters of such phenols, because they are easily subject to hydrolysis and therefore gradually release the phenols, which explains their prolonged effectiveness but also their time-related loss of effectiveness. The subsequent binding of the phenols hydrolytically released by amino organosilane esters, however, appears to be impossible or possible to only a limited extent, as shown by comparative tests in which the substances of the invention likewise appear to be superior, apparently because the free amino groups react away in some other manner during use and are no longer available.

As a result of their properties, the substances of the invention are advantageously suitable for the preservation of materials against biological pests, such as molds, algae, decay bacteria, disease-causing agents and chewing insects, wherever formerly no satisfactory solutions have been found due to the difficulties described above, as for example in the treatment of wood, textiles, paper, plastics, varnishes, lacquers and paints, mineral fillers and surfaces for longterm preservation against biological attack or infection.

For example, they are suitable for preservative and disinfectant treatment against rot, mold, consumption by insects, the growth of algae and moss and the like on construction lumber (e.g., wood structure, assemblies, roof trusses, gates, paneling, raftered ceilings, etc.), railroad thresholds, posts and masts, boats, docks, and the like.

In the textile field, effective protection can be given not only to natural fibers such as linen, cotton, jute, wool, silk and cellulose products as well as leather, but also to synthetic fibers such as textiles on a basis of polyamide, polyester, nitrile and urethane; also, fishing nets, tarpaulins, floor and wall coverings, covers and curtains, germ-free clothing, and so forth.

Plastic products suitable for biocidal treatment with the substances of the invention are thermoplastics such as polyvinyl halides, polyolefins, polyesters and polyamides (as well as copolymers thereof and molding compositions containing them), such as polyvinyl chloride, polyvinylidene fluoride, low-pressure and high-pressure polyethylene, polypropylene, polystyrene, polyacrylates, polytetramethylene terephthalate, polyacrylonitrile, acrylonitrile-butadienestyrene copolymers etc.; protection can also be given to natural and synthetic types of rubber, phenolic and urea resins, polyurethanes, casting risins such as epoxy and polyester resins, etc.

Suitable varnishes and paints are, for example, epoxy resin varnishes and polyester varnishes, zinc dust paints on the basis of polyethylsilicate, and dispersion paints.

Mineral substances, such as glass, glass fiber textiles, porcelain, sand, masonry and concrete surfaces, oxidic metal surfaces and the like can also be protected germicidally and/or against infestation by algae, mollusks and snails (for example in underwater construction).

The impregnation of wood, textiles and mineral substances is best performed by immersion optionally in vacuo brushing or spraying with solutions of the substances of the invention in solvents such as alcohols, hydrocarbons or chlorinated hydrocarbons, together, if desired, with other substances such as water repellents, adhesivizers or paints, including also emulsions containing such compositions. In the case of plastics, their incorporation, together with other additives if desired, such as dyes, light and heat stabilizers, fire retardants, pigments, working adjuvants, plasticizers, fillers, fiber reinforcements etc., by methods commonly used in the plastics art, without requiring special measures.

In the case of liquid preparations such as casting resins, varnishes and paints, incorporation simply by mixing suffices.

The substances of the invention are easily compatible as additives in polymers and have the characteristics of extenders. The subsequent fabrication of the compounds to produce, for example, floor coverings, decorative panels, extrusions, cable jacketing, coatings, tubing, injection moldings, laminates, granules, sheet materials and pressings can be performed in the conventional manner on the machines available for the purpose, and it is not impaired by the additives of the invention.

EXAMPLES

The following examples of preparation and application as well as those given for purposes of comparison will serve to explain the invention without, however, limiting its scope.

EXAMPLE 1

Preparation of
3-N,N-dimethylaminopropyltrimethoxysilane pentabromo hydrogen phenolate In a two-liter three-necked flask equipped with a jacket, stirrer, internal thermometer, dropping funnel and reflux condenser, 488.9 g of pentabromophenol (M.P. 225° C.) is suspended in 900 ml of trans-dichloroethylene. Over a period of 30 minutes, 207.2 g of 3-N-N-dimethylaminopropyltrimethoxysilane is added drop by drop while cooling the reaction flask with water and stirring; the pentabromophenol passes smoothly into solution and the temperature of the reaction solution rises from 21° C. to 33° C. Then the transdichloroethylene is distilled off at 48° C. through a simple distillation attachment, ultimately in vacuo, and finally the reaction product is freed of solvent residue at 48° C. and 0.1 Torr. No free methanol can be detected in the distillate or in the product.

The 3-N,N-dimethylaminopropyltrimethoxysilanepentabromo hydrogen phenolate is a viscous, pale yellow oil, $D_4^{20}=1.371$, $n_C^{25}=1.5910$. Weight 695 grams.

Elemental analysis ($C_{14}H_{22}Br_5NO_4Si$, M. 695.96):

|  | C | H | Br | N | Si |
|---|---|---|---|---|---|
| Calculated | 24.18% | 3.19% | 57.40% | 2.02% | 4.05% |
| Found | 24.31% | 3.40% | 57.21% | 1.84% | 3.92% |

Neither of the starting substances is detectable by gas chromatography. The phenolic hydroxy absorptions are considerably shifted in the infrared spectrum (broad band at approximately 2300 cm$^{-1}$) and in the NMR spectrum ($\sim = 12.46$ ppm; integral 0.9), due to a very strong formation of hydrogen bridges of the kind found in salt-like charge transfer (1:1) complex compounds.

EXAMPLE 2

Preparation of
3-N,N-dimethylaminopropyltrimethoxysilane pentachloro hydrogen phenolate In a manner similar to Example 1, 533 g of pentachlorophenol (M.P. 189° C.) is suspended in 900 ml of gasoline (B.P. 63°–80° C.) and over a period of 30 minutes it was reacted with 414.4 g of 3-N,N-dimethylaminopropyltrimethoxysilane, the pentachlorophenol passing smoothly into solution and the temperature in the reaction solution rising from 18° C. to 39° C. Then the gasoline is distilled out at 80° with a simple distillation attachment, ultimately in vacuo, and finally the reaction product is freed of the solvent at 80° C. and 0.1 Torr. No free methanol is detectable in the distillate or in the product.

The 3-N,N-dimethylaminopropyltrimethoxysilane pentachloro hydrogen phenolate is a viscous, light brown oil, $D_4^{20}=1,089$; $n_D^{25}=1.5454$. Weight 948 g.

Elemental analysis ($C_{14}H_{22}Cl_5NO_4Si$, Mol. wt. 473.69):

|  | C | H | Cl | N | Si |
|---|---|---|---|---|---|
| Calculated | 35.53% | 4.67% | 37.42% | 2.96% | 5.72% |
| Found | 35.80% | 4.79% | 37.14% | 2.80% | 5.70% |

EXAMPLE 3

Reaction of
3-N,N-dimethylaminopropyltrimethoxysilane with a mixture consisting of 84% of pentachlorophenol and 16% of 2,3,4,6-tetrachlorophenol.

In a kettle equipped with an anchor stirrer and a distillation attachment and having a capacity of 700 liters, 261 kg of a mixture of 84% of pentachlorophenol and 16% of 2,3,4,6-tetrachlorophenol is placed together with 50 kg of methanol. With stirring and the passing of cooling water through the jacket of the kettle, 207.2 kg of 3-N,N-dimethylaminopropyltrimethoxysilane mixed with 50 kg of methanol was fed in over a period of 90 minutes, the chlorophenol mixture passing smoothly into solution and the temperature of the reaction mixture rising from 20° C. to 34° C. Then a distillation was performed at about 60° C. and finally the reaction product was freed of solvent residue at 1 Torr.

The adduct is a viscous, light brown oil; $D_4^{20}=1.083$; $n_D^{25}=1.5393$; weight 466 kg.

Elemental analysis: (84% $C_{14}H_{22}Cl_5NO_4Si + 16\%$ $C_{14}H_{23}Cl_4NO_4Si$; $\overline{M}$. 468.18)

|  | C | H | Cl | N | Si |
|---|---|---|---|---|---|
| Calculated | 35.9% | 4.8% | 36.7% | 3.0% | 6.0% |
| Found | 36.1% | 4.9% | 36.5% | 2.8% | 5.9% |

EXAMPLE 4

Reaction of 3-aminopropyltrimethoxysilane with 2,4,6-trinitrophenol (picric acid)

Similarly to Example 1, 45.8 g of picric acid was reacted for 10 minutes with 44.2 g of 3-aminopropyltriethoxysilane in the presence of 50 ml of trans-dichloroethylene without cooling. A clear, yellow solution forms, while the internal temperature rises from 20° C.

to 47° C. Upon the withdrawal of the solvent a yellow crystallizate forms having a melting point of 76° C. Weight of product 90 g.

Elemental analysis ($C_{15}H_{27}N_4O_{10}Si$; Mol. Wt. 450.49):

|  | C | H | N | Si |
|---|---|---|---|---|
| Calculated | 32.7% | 6.04% | 12.4% | 6.2% |
| Found | 32.7% | 6.1% | 12.2% | 6.3% |

EXAMPLE 5

Reaction of 3-aminopropyltriethoxysilane with p-cresol.

Similarly to Example 4, 21.6 g of p-cresol was reacted without solvent with 44.2 g of 3-aminopropyltriethoxysilane with water cooling for a period of 10 minutes, the temperature rising from 22° C. to 29° C. 65 g of adduct was obtained as a pale red liquid; $D_4^{20} = 1.009$; $n_D^{25} = 1.4766$.

The gas chromatogram contains no p-cresol and a trace of 3-aminopropyltriethoxysilane; no ethanol or any corresponding cresyl silane ester can be detected.

Elemental Analysis ($C_{16}H_{31}NO_4Si$; 329.52):

|  | C | H | N | Si |
|---|---|---|---|---|
| Calculated: | 58.3% | 9.5% | 4.25% | 8.5% |
| Found: | 58.2% | 9.7% | 4.1% | 8.5% |

EXAMPLE 6

Reaction of 3-aminopropyltriethoxysilane with 2,4-dichlorophenol

In a manner similar to Example 4, 32.6 g of 2,4-dichlorophenol is reacted without cooling in 50 ml of methylene chloride, the internal temperature rising from 21° to 42° C. 76 g of adduct is obtained as a pale yellowish brown, viscous oil; $D_4^{20} = 1.126$; $n_D^{25} = 1.5056$.

Elemental analysis ($C_{15}H_{26}Cl_2NO_4Si$; M. 384.39):

|  | C | H | Cl | N | Si |
|---|---|---|---|---|---|
| Calculated: | 46.9% | 7.1% | 18.4% | 3.6% | 7.3% |
| Found: | 47.0% | 7.3% | 18.4% | 3.5% | 7.3% |

EXAMPLE 7

Reaction of 3-aminopropyltriethoxysilane with pentachlorophenol

In a paddle dryer of 1000 liters capacity equipped with a distillation apparatus, 266.5 kg of pentachlorophenol was combined with 200 liters of gasoline (B.P 63°-80° C.). With stirring, and with cooling water flowing through the jacket of the paddle dryer, 221 kg of 3-aminopropyltriethoxy silane is fed into it over a period of 60 minutes, while the reaction temperature is maintained at about 28° C. The pentachlorophenol reacts quantitatively with the formation of a suspension of the aminosilane adduct. The product is worked up as in Example 3, and 485 kg is obtained of a white crystalline powder having a melting point of 107° C.

Elemental analysis ($C_{15}H_{24}Cl_5NO_4Si$; M. 487.74):

|  | C | H | Cl | N | Si |
|---|---|---|---|---|---|
| Calculated: | 37.2% | 5.0% | 36.3% | 2.9% | 5.7% |
| Found: | 37.4% | 5.2% | 36.2% | 2.7% | 5.9% |

EXAMPLE FOR COMPARISON WITH EXAMPLE 7

Reaction of 3-aminopropyltriethoxysilane with pentachlorophenol in the presence of triethylamine;

In a 250 ml three-necked flask equipped with magnetic stirrer, reflux condenser and dropping funnel, 26.6 g of pentachlorophenol is placed for dissolving in 70 ml of chloroform and 50 ml of triethylamine. Over a period of 10 minutes, 22.1 g of 3-aminopropyltriethoxysilane is added, drop by drop, with refluxing and stirring. After three hours of boiling and stirring, the clear solution is concentrated by distilling out the chloroform, the ethanol that is formed, and most of the triethylamine, and the product is carefully precipitated with 130 ml of pentane, with stirring. It is washed thrice with pentane and decanted, then dried in a high vacuum at about 60° C. 41 g of a finely divided 3-aminopropyldiethoxypentachlorophenoxysilane is obtained having a melting point of 122° C.

The mixed melting point with the adduct of Example 7 of the invention is 84°-86° C.

Elemental analysis ($C_{13}H_{18}Cl_5NO_3Si$; M. 441.67):

|  | C | H | Cl | N | Si |  |
|---|---|---|---|---|---|---|
| Calculated: | 35.4% | 4.1% | 40.2% | 3.2% | 6.3% | Fo |
| Found: | 35.3% | 4.2% | 40.4% | 3.3% | 6.3% |  |

EXAMPLE 8

Reaction of 3-aminopropyltriethoxysilane with a mixture consisting of 84% pentachlorophenol and 16% 2,3,4,6-tetrachlorophenol.

In a manner similar to Example 1, 522 g of a mixture of 84% pentachlorophenol and 16% 2,3,4,6-tetrachlorophenol was reacted in 800 ml of ethanol with 442 g of 3-aminopropyltriethoxysilane. After the withdrawal of the ethanol, 960 g of powdery, white adduct is obtained, having a melting point of 83° C.

Elemental analysis (84% $C_{15}H_{24}Cl_5NO_4Si$ + 16% $C_{15}H_{25}Cl_4NO_4Si$; $\overline{M}$. 482.21):

|  | C | H | Cl | N | Si |
|---|---|---|---|---|---|
| Calculated: | 37.4% | 5.1% | 35.6% | 2.9% | 5.8% |
| Found: | 37.5% | 5.2% | 35.4% | 2.7% | 5.8% |

EXAMPLE 9

Reaction of 2-(2'-aminoethylamino)-ethyltriethoxysilane with a mixture consisting of 84% pentachlorophenol and 16% 2,3,4,6-tetrachloro phenol.

In a manner similar to Example 1, 522 g of a mixture of 84% pentachlorophenol and 16% 2,3,4,6-tetrachlorophenol was reacted in 900 ml of chloroform with 250 g of 2-(2'-amino)-ethyltriethoxysilane. After withdrawal of the chloroform there remains a light brown oil which within about 3 hours crystallizes completely to a white crystallizate having a melting point of 48° C.

Elemental analysis (84% $C_{22}H_{28}Cl_{10}N_2O_5Si$ + 16% $C_{22}H_{30}Cl_8N_2O_5Si$; $\overline{M}$. 772.08):

|  | C | H | Cl | N | Si |
|---|---|---|---|---|---|
| Calculated: | 34.3% | 3.7% | 44.4% | 3.6% | 3.6% |
| Found: | 34.4% | 3.7% | 44.2% | 3.5% | 3.4% |

EXAMPLE 10

Reaction of N-cyclohexylaminomethyldimethylethoxysilane with pentachlorophenol In a manner similar to Example 4, 26.6 g of pentachlorophenol was reacted with 21.5 g of N-cyclohexylaminomethyldimethylethoxysilane. Upon withdrawal of the solvent, 48 g of white adduct crystallizes, having a melting point of 176° C.

Elemental analysis ($C_{17}H_{26}Cl_5NO_2Si$; $\overline{M}$. 481.78):

|  | C | H | Cl | N | Si |
|---|---|---|---|---|---|
| Calculated: | 42.4% | 5.5% | 36.8% | 2.9% | 5.8% |
| Found: | 42.4% | 5.7% | 36.5% | 2.7% | 5.9% |

EXAMPLE 11

Reaction of 3-N-methylaminopropyltrimethoxysilane with pentachlorophenol.

In a manner similar to Example 1, 533 g of pentachlorophenol is reacted with 386.6 g of 3-N-methylaminopropyltrimethoxysilane.

In the refinement of the product, 920 g of a white adduct crystallizes, having a melting point of 89° C.

Elemental analysis ($C_{13}H_{20}Cl_5NO_4Si$; $\overline{M}$. 459.68):

|  | C | H | Cl | N | Si |
|---|---|---|---|---|---|
| Calculated: | 33.9% | 4.4% | 38.5% | 3.0% | 6.1% |
| Found: | 34.1% | 4.6% | 38.5% | 3.0% | 6.0% |

EXAMPLES 12–20

Effective concentrations of the active substances of the invention against bacteria and fungi Cultures of bacteria and fungi are used to determine the minimum concentrations of the dissolved substances which are necessary in order to kill bacteria or fungi. Table I shows the findings.

TABLE I*

Effective concentrations, expressed in percent, against test organisms.

| Ex. No. | Substance | | Esch. coli | Staph. aureus | Asp. niger |
|---|---|---|---|---|---|
| 12 | 3-N,N—dimethylaminopropyl trimethoxysilane-pentabromophenol adduct | Acetone | 0.012 | 0.0024 | 0.06 |
| 13 | 3-N,N—dimethylaminopropyltrimethoxysilane-pentachlorophenol adduct | acetone | 0.012 | 0.00048 | 0.0024 |
| 14 | 3-N—methylaminopropyltrimethoxysilane pentachlorophenol adduct | acetone | 0.012 | 0.00048 | 0.0024 |
| 15 | 2-N—(2'-aminoethyl)-aminoethyltriethoxysilane-bis-pentachlorophenol adduct | acetone | 0.012 | 0.00048 | 0.0024 |
| 16 | 3-aminopropyl triethoxysilane-pentachlorophenol adduct | acetone | 0.06–0.012 | 0.0024 | 0.012–0.0024 |
| 17 | N—cyclohexylaminomethyl dimethylethoxysilane-pentachlorophenol adduct | methanol | 0.03 | 0.012–0.0024 | 0.012–0.0024 |
| 18 | pentachlorophenol sodium (for comparison) | water | 0.06 | 0.012 | 0.012 |
| 19 | 3-aminopropyldiethoxypentachlorophenoxysilane (for comparison) | acetone | 0.03–0.06 | 0.06–0.012 | 0.06–0.012 |
| 20 | Solution of 5 wt.-% of pentachlorophenol and 10 wt.-% of 3-aminopropyltriethoxysilane in 2-butoxyethanol containing about 0.5% water (for comparison) | | 0.06 | 0.012 | 0.012 |

*The substances analogous to Examples 13, 14, 15 and 16 and containing 84% pentachlorophenol and 16% tetrachlorophenol in the adduct produce numerically equal results.

EXAMPLES 21–28

Agar diffusion test of the active substances of the invention against Aspergillus niger 0.1 ml of a test solution of the effective concentration given in Table I is placed in the center of an agar culture of Aspergillus niger and the diameter of the fully developed zone of effect is measured. Table II lists the findings.

TABLE II**

Diameter of the zones of effect against *Aspergillus niger*

| Ex. No. | Substance | Diam. of the effective zone |
|---|---|---|
| 21 | 3-N,N—dimethylaminopropyl-trimethoxysilane-pentachlorophenol adduct | 50 (also, no formation of spores anywhere on the culture surface.) |
| 22 | 3-N—methylaminopropyl-trimethoxysilane-pentachlorophenol adduct | 60 (also, no formation of spores anywhere on the culture surface.) |
| 23 | 2-N—(2'-aminoethyl)-aminoethyltriethoxysilane-bis-pentachlorophenol adduct | 47 (also, no formation of spores anywhere on the culture surface.) |
| 24 | 3-aminopropyltriethoxysilane-pentachlorophenol adduct | 38 (also, no formation of spores anywhere on the culture surface.) |
| 25 | N—cyclohexylaminomethyl-dimethylethoxysilane-pentachlorophenol adduct | 22 (also, no formation of spores anywhere on the culture surface.) |
| 26 | Pentachlorophenol (in acetone) (for comparison) | 21 — |
| 27 | 3-aminopropyldiethoxypentachlorophenoxysilane (for comparison) | 18 — |
| 28 | Mixture from Example 20 (cf. TABLE I) | 27 — |

TABLE II**-continued

Diameter of the zones of effect against *Aspergillus niger*

| Ex. No. | Substance | Diam. of the effective zone |
|---|---|---|
| (for comparison) | | |

**The substances analogous to Examples 21, 22, 23 and 24 containing 84% pentachlorophenol and 16% tetrachlorophenol in the adduct produce slightly larger effective zone measurements.

EXAMPLES 29–36

Long term tests in polyethylene

In a kneader, at 120° C., 0.1% of 3-N,N-dimethylaminopropyltrimethoxysilane (84% pentachlorophenol + 16% tetrachlorophenol) adduct (A) was incorporated into commercial high-pressure polyethylene and sheets 1 mm thick were pressed from the resulting compound.

The same procedure was employed with 3-aminopropyltriethoxysilane-pentachlorophenol adduct (B) and also, for comparison, 3-aminopropyldiethoxypentachlorophenoxysilane (C) and pentachlorophenol (D).

The entomological test was performed by permanent contact and force-feeding tests with imagos of *Calandra granaria*, workers of *Reticulitermes santonensis* and mature larvae of *Kalotermes flavicollis* (for results see Table III).

The bacteriological test was performed on *Staphylococcus aureus* and the fungus test on *Candida albicans*. Strips 4 cm long and ½ cm wide were let lie for two days in sterile Petri dishes. After testing for sterility, the strips were immersed each in 15 ml of culture suspension or solution, dabbed sterile, set aside in Petri dishes, then transferred each into 10 ml of nutrient solution about one day later, and observed for growth (see Table IV for results).

For climatization before the test, part of the sheet material is let stand for 2 months in a stream of fresh air whose temperature and relative humidity is set at 40° C. and 50% for 16 hours and then at 20° C. and 70% for 8 hours, repeated daily (for results see Table IV).

TABLE III[1]

Insect tests (permanent contact and forced feeding tests) on repellentized high-pressure polyethylene.

| | Calandra | | Reticulitermes | | Kalotermes | |
|---|---|---|---|---|---|---|
| Example No. | after incorporation | after climatization | after incorporation | after climatization | after incorporation | after climatization |
| 29 (A) | − | − | −(0) | −(0) | − | − |
| 30 (B) | − | − | −0 | −0 | − | − |
| 31 (C) (for comparison) | − | + | −0 | + | − | + |
| 32 (D) (for comparison) | (+) | + | (+) | + | + | + |
| Blank test (untreated high-pressure polyethylene) | + | + | + | + | + | + |

[1] + = insect damage
− = no sign of insect damage
0 = insecticidal effects;
A = 0.1% adduct of 3-N,N—dimethylaminopropyltrimethoxysilane and 84% pentachlorophenol + 16% tetrachlorophenol.
B = Adduct of 3-aminopropyltriethoxysilane and pentachlorophenol;
C = 3-aminopropyldiethoxypentachlorophenoxysilane;
D = pentachlorophenol

TABLE IV[2]

Bactericidal and fungicidal tests on treated high-pressure polyethylene.

| | Staphyloccus aureus | | Candida albicans | |
|---|---|---|---|---|
| Example | after incorporation | after climatization | after incorporation | after climatization |
| 33 (A) | − | − | − | − |
| 34 (B) | − | − | − | − |
| 35 (C) (for comparison) | − | + | − | + |
| 36 (D) (for comparison) | (+) | + | (+) | + |
| Blank test (untreated high-pressure polyethylene) | + | + | + | + |

[2] + = growth occurred
− = no growth occurred
A, B, C, D - see footnote to Table III.

EXAMPLE 37

Test for effectiveness against the growth of algae

A commercial anticorrosive varnish on the basis of zinc dust and ethyl polysilicate 40 is treated with 0.1% of an adduct of 3-N-methylaminopropyltrimethoxysilane (84% pentachlorophenol + 16% tetrachlorophenol) in the form of a 50% solution in ethanol. The varnish thus treated is applied to test pieces of sheet steel measuring 200×40 mm, and cured. For comparison, test pieces of steel coated with the untreated varnish were used. After two months of exposure to a green algae culture, the untreated test pieces are overgrown with algae while those coated with the varnish treated with the substance of the invention are free of algae.

What is claimed is:

1. A process for preserving a material against biological attack and/or biological infection and/or biological infestation caused by fungi, bacteria, viruses, microphytes (e.g., algae), insects and other microorganisms which comprises applying thereto an effective amount of an adduct of phenol with an aminoorganosilane ester with salt-like charge-transfer-complex structure of the general formula

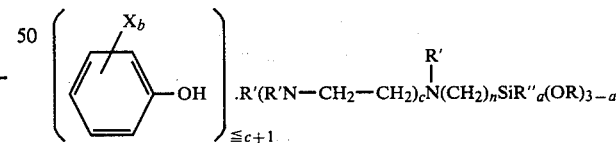

wherein
R represents an alkyl moiety of 1 to 8 carbon atoms or ethylene glycol or propylene glycol or up to 3 polyethylene or polypropylene glycol moieties terminally closed with a lower alkyl or acyl group of a lower alkanoic acid;
R' represents hydrogen or alkyl moieties having 1 to 20 carbon atoms optionally containing one or more ether bridges or a cyclohexyl moiety;
R" represents alkyl with 1 to 8 carbon atoms;
X represents halogen or $C_{1-4}$ alkyl moieties or a nitro group;
a being a value of 0 to 3;

b a value of 0 to 5;
c a value of 0 to 20; and
n a value of 1 to 6.

2. A process according to claim 1, wherein the adduct has the formula

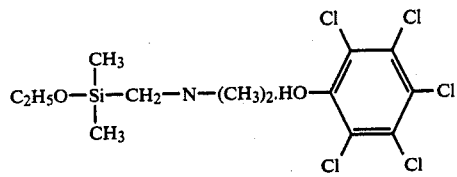

3. A process according to claim 1, wherein the adduct has the formula

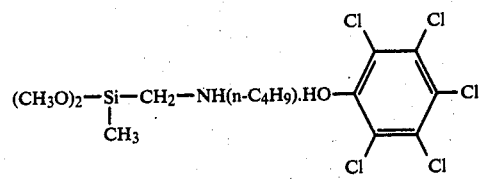

4. A process according to claim 1, wherein the adduct has the formula

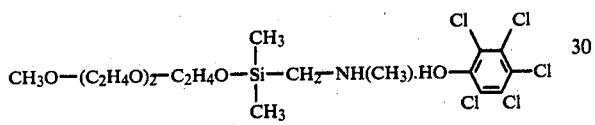

5. A process according to claim 1, wherein the adduct has the formula

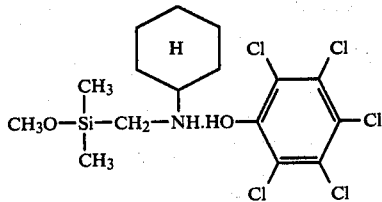

6. A process according to claim 1, wherein the adduct has the formula

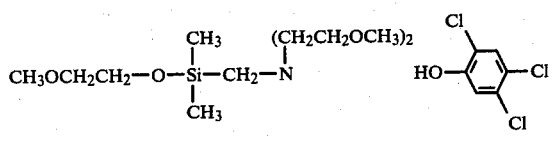

7. A process according to claim 1, wherein the adduct has the formula

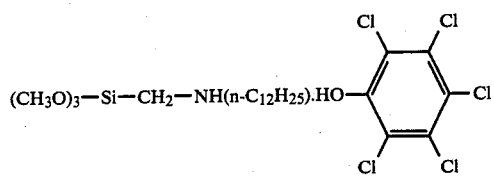

8. A process according to claim 1, wherein the adduct has the formula

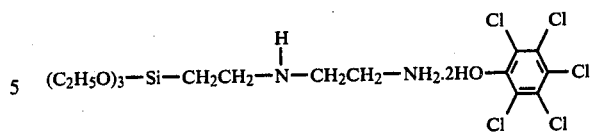

9. A process according to claim 1, wherein the adduct has the formula

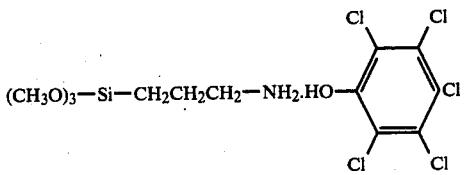

10. A process according to claim 1, wherein the adduct has the formula

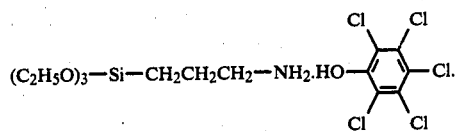

11. A process according to claim 1, wherein the adduct has the formula

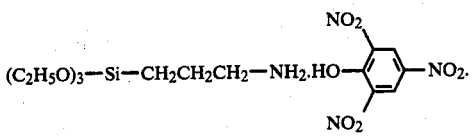

12. A process according to claim 1, wherein the adduct has the formula

13. A process according to claim 1, wherein the adduct has the formula

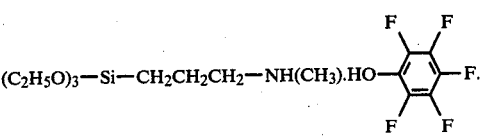

14. A process according to claim 1, wherein the adduct has the formula

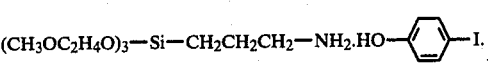

15. A process according to claim 1, wherein the adduct has the formula

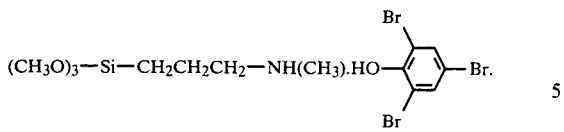

16. A process according to claim 1, wherein the adduct has the formula

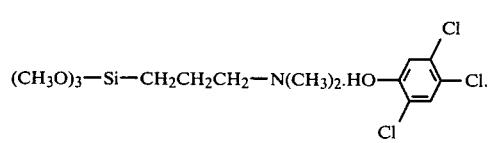

17. A process according to claim 1, wherein the adduct has the formula

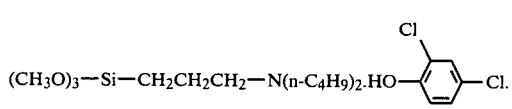

18. A process according to claim 1, wherein the adduct has the formula

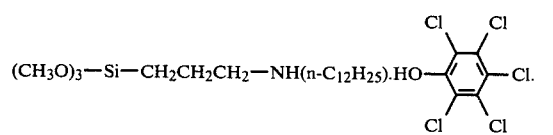

19. A process according to claim 1, wherein the adduct has the formula

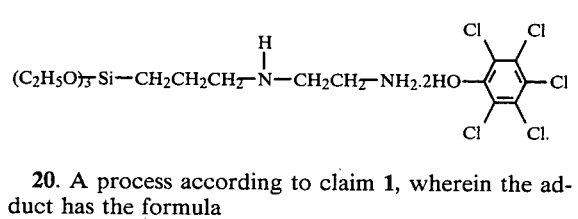

20. A process according to claim 1, wherein the adduct has the formula

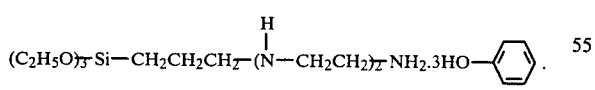

21. A process according to claim 1, wherein the adduct has the formula

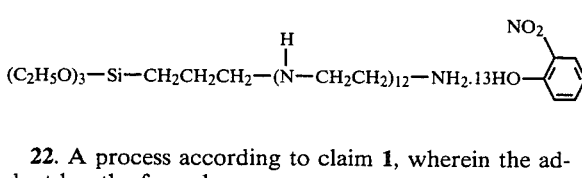

22. A process according to claim 1, wherein the adduct has the formula

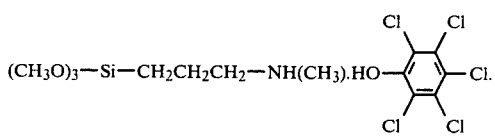

23. A process according to claim 1, wherein the adduct has the formula

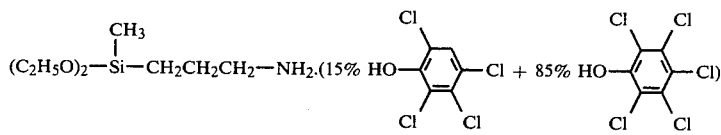

24. A preservative composition for materials against biological attack and/or biological infection and/or biological infestation caused by fungi, bacteria, viruses, microphytes (e.g. algae), insects and other microorganisms which comprises an inert diluent and an effective amount of an adduct of phenol with an aminoorganosilane ester with salt-like charge-transfer-complex structure of the general formula

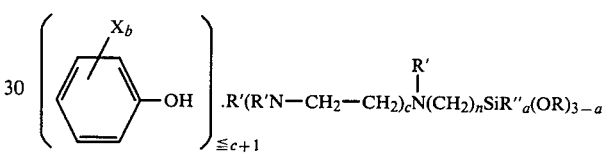

wherein

R represents an alkyl moiety of 1 to 8 carbon atoms or ethylene glycol or propylene glycol or up to 3 polyethylene or polypropylene glycol moieties terminally closed with a lower alkyl or acyl group of a lower alkanoic acid;

R' represents hydrogen or alkyl moieties having 1 to 20 carbon atoms optionally containing one or more ether bridges or a cyclohexyl moiety;

R" represents alkyl with 1 to 8 carbon atoms;

X represents halogen or $C_{1-4}$ alkyl moieties or a nitro group;

a being a value of 0 to 3;

b a value of 0 to 5;

c a value of 0 to 20; and n a value of 1 to 6.

25. A preservative according to claim 24, wherein the adduct has the formula

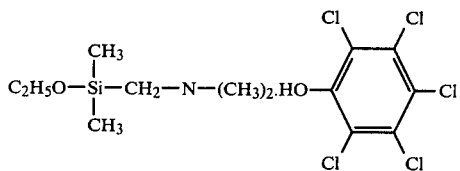

26. A preservative according to claim 24, wherein the adduct has the formula

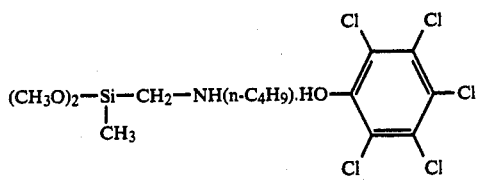

27. A preservative according to claim 24, wherein the adduct has the formula

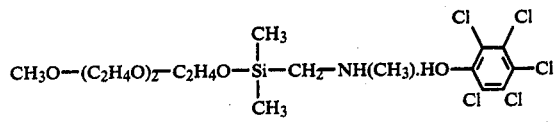

28. A preservative according to claim 24, wherein the adduct has the formula

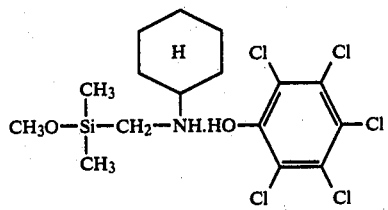

29. A preservative according to claim 24, wherein the adduct has the formula

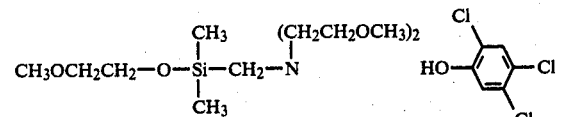

30. A preservative according to claim 24, wherein the adduct has the formula

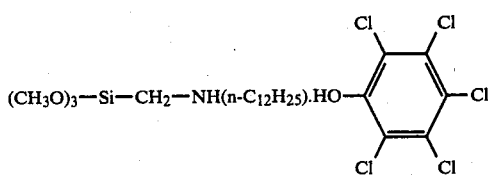

31. A preservative according to claim 24, wherein the adduct has the formula

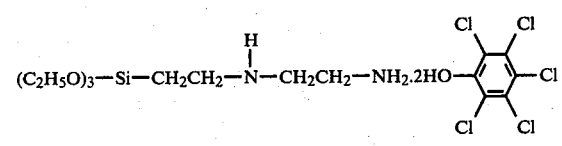

32. A preservative according to claim 24, wherein the adduct has the formula

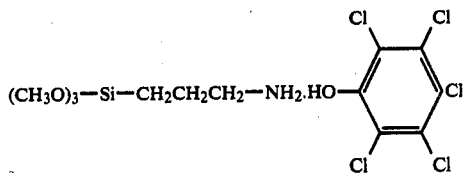

33. A preservative according to claim 24, wherein the adduct has the formula

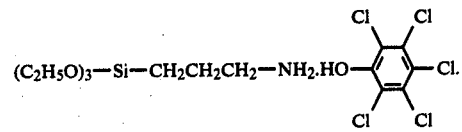

34. A preservative according to claim 24, wherein the adduct has the formula

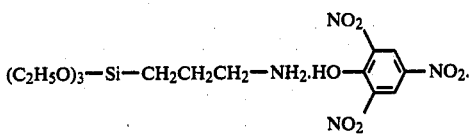

35. A preservative according to claim 24, wherein the adduct has the formula

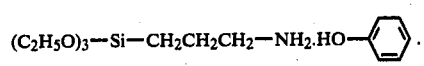

36. A preservative according to claim 24, wherein the adduct has the formula

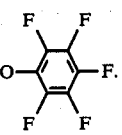

37. A preservative according to claim 24, wherein the adduct has the formula

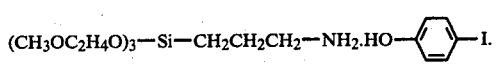

38. A preservative according to claim 24, wherein the adduct has the formula

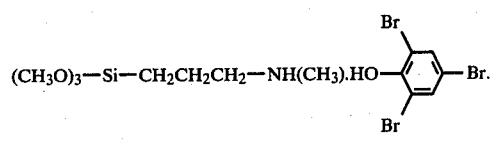

39. A preservative according to claim 24, wherein the adduct has the formula

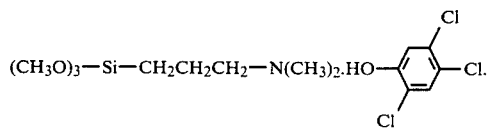

40. A preservative according to claim 24, wherein the adduct has the formula

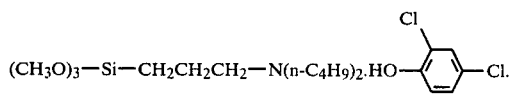

41. A preservative according to claim 24, wherein the adduct has the formula

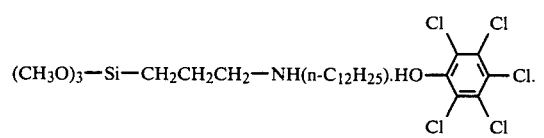

42. A preservative according to claim 24, wherein the adduct has the formula

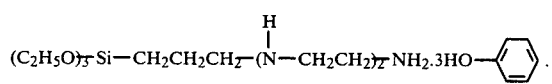

43. A preservative according to claim 24, wherein the adduct has the formula $(C_2H_5O)_3\text{-Si-CH}_2CH_2CH_2\text{-(N-CH}_2CH_2)_2\text{-NH}_2 \cdot 3HO$—⟨⟩.

44. A preservative according to claim 24, wherein the adduct has the formula

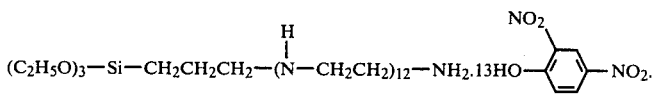

45. A preservative according to claim 24, wherein the adduct has the formula

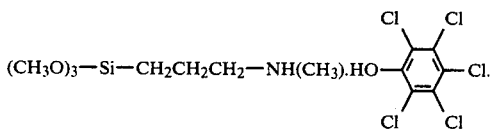

46. A preservative according to claim 24, wherein the adduct has the formula

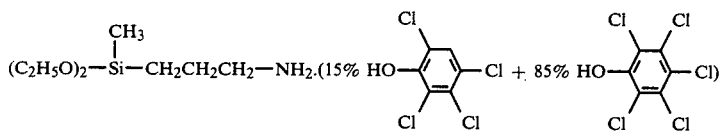

* * * * *